United States Patent [19]

Lynch et al.

[11] Patent Number: 4,952,288

[45] Date of Patent: Aug. 28, 1990

[54] PROCESS FOR THE PREPARATION OF 4-ACYLOXYAZETIDIN-2-ONE BY ELECTROCHEMICAL METHODS

[75] Inventors: Joseph E. Lynch, Plainfield; Ralph P. Volante, East Windsor, both of N.J.; William L. Laswell, Perkasie, Pa.; Ichiro Shinkai, Westfield, N.J.

[73] Assignee: Merck & Co., Inc., Rahway, N.J.

[21] Appl. No.: 369,167

[22] Filed: Jun. 21, 1989

[51] Int. Cl.$^5$ .............................................. C25B 3/00
[52] U.S. Cl. .................................. 204/59 R; 340/200; 340/357
[58] Field of Search ............. 540/357, 200; 204/59 R

[56] References Cited

U.S. PATENT DOCUMENTS

| | | | |
|---|---|---|---|
| 3,953,499 | 4/1976 | Pike et al. | 562/503 |
| 4,260,618 | 4/1981 | Christensen | 514/192 |
| 4,791,207 | 12/1988 | Salzmann et al. | 548/110 |

FOREIGN PATENT DOCUMENTS 0167155 8/1986 European Pat. Off.
J6 1243-079-A 1/1985 Japan.

OTHER PUBLICATIONS

Stuart L. Schreiber et al., Tetrahedron Ltrs., vol. 24, No. 23, pp. 2363–2366, 1983.
Bruce H. Lipshutz, Chem. Rev. 1986, 86,795–819.
Maria Altamura et al., Syn. Comm., 18(16–17), 2129–2133, (1988).
Klaus Gollnick et al., Tetrahedron, vol. 41, No. 11, pp. 2057 to 2068, 1985.
Masao Shiozaki et al., Tetrahedron, vol. 40, No. 10, pp. 1795 to 1802, 1984.
Paul J. Reider et al., Tetrahedron Lts., vol. 23, No. 22, pp. 2293–2296, 1982.
Curt Wentrup et al., J. Am. Chem. Soc. 1980, 102, 6161–6163.
Gunda I. Georg et al., Tetrahedron Ltrs., vol. 26, No. 33, pp. 3903–3906, 1985.
Gunda I. Georg et al., J. Am. Chem. Soc. 1987, 109, 1129–1136.

Primary Examiner—John F. Niebling
Assistant Examiner—Steven P. Marquis
Attorney, Agent, or Firm—John W. Harbour; Hesna J. Pfeiffer

[57] ABSTRACT

The 4-acryloxyazetidin-2-ones, which are intermediates in the production of carbapenems and penems, are produced from 4-furanylazetidin-2-ones by electrochemical methods.

10 Claims, No Drawings

PROCESS FOR THE PREPARATION OF 4-ACYLOXYAZETIDIN-2-ONE BY ELECTROCHEMICAL METHODS

The present invention relates to the preparation of 4-acyloxyazetidin-2-ones. More particularly, the present invention relates to the preparation of the above compounds through a 4-furan-2-ylazetidin-2-one intermediate.

BACKGROUND OF THE INVENTION

Carbapenems and penems are well known antibiotics for treating a broad range of gram-negative and gram-positive bacterial infections.

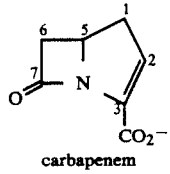
carbapenem

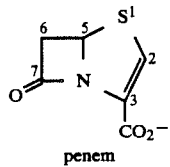
penem

Methods and intermediates for the manufacture of carbapenems and penems are thus matters of scientific and commercial importance.

One method for the production of carbapenems is described in GB No. 2,162,840, Cainelli, et al. As described therein, certain carbapenems are produced from 4-acetoxyazetidin-2-one intermediates.

These intermediates are in turn produced in a multistep synthesis from 4-alkenylazetidin-2-one intermediates of the formula:

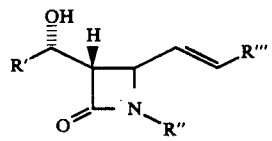

The starting materials to produce the 4alkenylazetidin-2-one intermediates are:

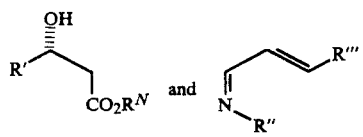

Thus, carbapenems may be produced through two principal intermediates from readily made or available starting materials. However, methods having fewer reaction steps to obtain the intermediates and improved yields are desirable.

Another method for the production of carbapenems is described in EPO No. 0167155, Kan, et al. Again, certain carbapenems are produced from 4-acetoxyazetidin-2-one intermediates. In this case however, these intermediates are in turn produced from 4-triorganosilyloxyazetidin-2-one intermediates of the formula

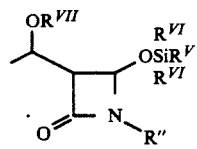

The starting materials to produce the 4-triorganosilyloxyazetidin-2-one intermediates are:

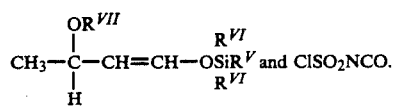

Thus, again, carbapenem may be produced through two principle intermediates from readily made or available starting materials. However, methods having fewer reaction steps to obtain the intermediates as well as methods using less hazardous starting materials than $ClSO_2NCO$ are desired.

A method for the production of penems is disclosed in Christensen, et al., U.S. Pat. No. 4,260,618 from 4-acetoxyazetidin-2-one intermediates. Herein, it is recommended that these intermediates be produced by cleaving penicillin which is produced by fermentation.

It is an object of the present invention to produce 4-acyloxyazetidin-2 one intermediates useful in the production of carbapenems.

It is a further object of the present invention to produce 4-acyloxyazetidin-2 -one intermediates from starting materials which are easily handled on account of their low levels of toxicity.

It is yet another object of the present invention to simplify the reactions required and improve the reaction yields in the production of 4-acyloxyazetidin 2-one intermediates.

It is still another object of the present invention to develop a method for the production of 4-acyloxyazetidin-2-one intermediates where an organic group is employed to protect the carbon in the 4-position of the azetidin-2-one and which subsequently may be converted to the 4-acyloxy substitution without replacement.

BRIEF DESCRIPTION OF THE INVENTION

Briefly, there is provided by the present invention a method for the production of 4-acyloxyazetidin-2-ones comprising the steps of:

(a) contacting, at temperatures from about 0°–20° C., an oxidizing combination of bromine and sufficient sodium chlorite to produce 4-carboxyazetidin-2-one with a 4-furanyl compound of the formula (I):

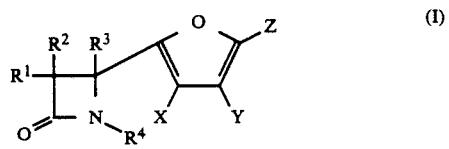

wherein $R^1$ and $R^2$ are independently selected from the group consisting of hydrogen, $C_{1-10}$ alkyl, $C_{1-10}$ fluoroalkyl, alpha-carbon substituted $C_{1-10}$ alkyl, alpha-carbon substituted $C_{1-10}$ fluoroalkyl, where the alpha-carbon substituent is selected from the group consisting of hydroxyl and protected hydroxyl; $R^3$ is selected from the group consisting of hydrogen and $C_{1-10}$ alkyl; $R^4$ is selected from the group consisting of hydrogen and a protecting group for nitrogen, and X, Y and Z are independently selected from the group consisting of hydrogen, halogen, $C_{1-10}$ alkyl, $C_6$ or $C_{10}$ aryl, substituted $C_6$ or $C_{10}$ aryl, $C_{1-10}$ alkoxy, and $C_6$ or $C_{10}$ aryloxy; and (b) contacting, in a polar organic solvent, said 4-carboxyazetidin-2-one with a mixture of $C_{1-8}$ organic acid and its corresponding alkali metal salt under sufficient current density to produce 4-acyloxyazetidin-2-one.

DETAILED DESCRIPTION OF THE INVENTION

Herein, $R^1$ and $R^2$ represent those hydrogen, alkyl, and substituted alkyl substituents useful as 6-position substitution on carbapenems or carbapenams. $R^1$ and $R^2$ include, for example, hydrogen, methyl, ethyl, propyl, isopropyl, butyl, isobutyl, $HO-CH_2-$, $CH_3CH(OH)-$, $(CH_3)_2C(OH)-$, $(CH_2)_2C(OH)-$, $CH_3CH_2CH(OH)-$, $CH_3CH_2CH_2CH(OH)-$, $CH_3CH_2CH(CH_3)(OH)-$, $CH_3CH(CH_3)CH(OH)-$, $CF_3CH(OH)-$, $CHF_2CH(OH)-$, $FCH_2CH(OH)-$, $CH_3CHF-$, $F_2CH-$, $F_3C-$, $CH_3CF_2-$, etc.

In preferred embodiments, either $R^1$ or $R^2$ is hydrogen and, in a more preferred embodiment, $R^2$ is beta-hydrogen and $R^1$ is any of the above, excepting hydrogen, in an alpha orientation. Most preferably, $R^1$ is an alpha oriented 1-hydroxyethyl and $R^2$ is a beta oriented hydrogen.

The protected hydroxy is known in the antibiotic art and refers to a hydroxyl group protected by a suitable protecting radical rendering it inactive during chemical reaction Of course the identity of this protecting radical will depend on the particular chemical reaction from which the hydroxyl group is being protected. A preferred protecting radical useful herein in the production of the desired 4-acyloxy-azetidin-2-one is dimethyl-t-butylsilyl (TBDMS). This protecting radical may suitable for subsequent reactions of the desired compound or may require replacement depending on the scheme selected to produce penem or carbapenem. Further protecting groups which might be employed include trimethylsilyl, benzyl, p-nitrobenzyl, p-nitrobenzylcarbonyl, diphenyl-t-butylsilyl, isopropyldimethylsilyl, phenyl, methyl, etc. Other protecting radicals for hydroxyl groups are known in the art (See T. W. Greene, *Protective Groups in Organic Synthesis* John Wiley & Sons, Inc., 1981).

$R^3$ may be selected from hydrogen, methyl, ethyl, propyl, etc. Preferably, $R^3$ is hydrogen and has a beta orientation.

As stated above, R4 may be hydrogen or a protecting radical for nitrogen. Suitable protecting radicals for nitrogen include dimethyl-t-butylsilyl, trimethylsilyl, diphenyl-t-butylsilyl, triphenylsilyl, p-nitrobenzyloxycarbonyl, benzyl, substituted benzyl; p-methoxyphenyl, etc. As above with the protecting radical for the hydroxyl group, the identity of any protecting radical and whether a protecting radical is at all necessary will depend on the chemical reactions from which the nitrogen group is being protected. For example, herein, the 4-furanylazetidin-2-one is produced by a suggested reaction between a furanyl substituted imine and the derivative of a carboxy compound. In such reaction, the nitrogen of the imine requires a protecting radical such as benzyl. The benzyl may be added to the nitrogen by well known reactions and subsequently replaced with another protecting group or with hydrogen as desired. It is a unique advantage of the process herein to produce 4-acyloxyazetidin-2-one from 4furanylazetidin-2-one that no protecting radical is necessary for the nitrogen. Thus, it is preferred in the 4-furanyl azetidin-2-one of formula (1) that $R^4$ is hydrogen. Protecting radicals for nitrogen groups are well known in the art (See also, T. W. Greene, *Protective Groups In Organic Synthesis*, John Wiley & Sons, Inc., 1981).

Suitable X, Y and Z are independently selected from any of hydrogen, methyl, ethyl, propyl, t-butyl, n-butyl, phenyl, p-chlorophenyl, hydroxy, methoxy, ethoxy, phenoxy, etc. Preferably, at least Z is hydrogen. More preferably, X, Y and Z are hydrogen. The principle consideration of selecting X, Y and Z is that they not interfere with the processes taught herein.

Flow sheets A and B depict a suggested synthesis for the starting material described in formula (I). Flow Sheet A depicts the manufacture of an imine. This imine of Flow Sheet A is reacted with a carboxyl derivative in Flow Sheet B to produce the 4furan-2-yl-azetidin-2-one starting material.

Referring to Flow Sheet A, an available or readily produced furfural 1 is condensed with an amine compound 2. In the case of such condensation, $R^4$ of compound 2 is not hydrogen. Preferably, of course, $R^4$ is a protecting radical for nitrogen and more preferably an organic aromatic protecting radical. Suitable as Compound 2 is benzylamine.

Referring to Flow Sheet B, compound 4 is a readily available or easily produced ester starting material having $R^1$ and $R^2$ substitution or precursors thereof. Suitable ester starting materials as compound 4 include methyl 3-hydroxypropanoate, methyl 3-hydroxypentanoate, methyl 3-hydroxy-4,4,4-trifluorobutanoate, methyl 3-fluorobutanoate, methyl 2-methyl-3-hydroxybutanoate, etc. Preferred is methyl 3-hydroxybutanoate. The nature of the ester group described as methyl is not critical and could be ethyl, propyl, etc.

As the first reaction step of Flow Sheet B, compound 4 is enolized by reaction with a base such as that prepard from n-butyllithium and diisopropylamine in tetrahydrofuran at about $-71°$ C. Subsequently and without isolation of the reaction product, the enolate is quenched by the addition of trimethylchlorosilane (TMSCl), again in tetrahydrofuran at about $-78°$ C., to produce a ketenesilylacetal, compound 5. In this reaction to produce compound 5, any unprotected hydroxy group on either $R^1$ or $R^2$ will be substituted with trimethylsilyl. This is a desirable result as a protecting group will later be necessary any unprotected hydroxy of $R^1$ or $R^2$. If another on any type protecting group is desired, it should be added to the hydroxy of compound 4 prior to enolization. If another silyl protecting group is desired, then appropriate replacement should be made for trimethylchlorosilane in the reaction of quenching the enolate.

As the second reaction step of Flow Sheet B, the imine, compound 3, is added to the ketenesilylacetal, compound 5 in dichloromethane at about $-20°$ C. in the presence of trimethylsilyltrifluoromethanesulfonate (TMSOTf). The resultant compound 6 contains $R^1$ through $R^3$ *functionality*, $R^4$ functionality restricted to protecting radical for nitrogen and the necessary functionality to close the azetidin-2-one ring. At this point or later in Flow Sheet B, the protecting radical for nitrogen, $R^4$, may be converted to hydrogen or some other protecting radical to provide the full spectrum of $R^4$ substitution. For example, a benzyl protecting radical for nitrogen may be substituted with hydrogen through a hydrochloride by hydrogenation ($H_2$/Pd/C) in the presence of HCl and subsequent reaction with sodium hydroxide. Replacement of benzyl with other Protecting radicals may be achieved by various methods known to persons skilled in the art.

As the third reaction of Flow Sheet B, compound 6 where $R^4$ is either hydrogen or protecting group for nitrogen according to the above, is saponified to remove the methyl ester and produced compound 7. The saponification is carried out in water, raising the pH to high levels with sodium hydroxide.

Finally, starting material 8 is produced by dehydrating compound 7 to close the azetidin-2-one ring. The dehydration is carried out in 2-propanol with $NaHCO_3$ and methane sulfonylchloride MeS—Cl. A Preferred starting material 8 contains an $R^1$ with hydroxy substitution. This hydroxy substitution should be protected as appropriate from reaction conditions in which the starting material 8 is to be employed. The most preferred starting material 8 is shown in Example 6 as compound E9.

Flow Sheet C depicts the process of the invention herein for producing 4-acyloxyazetidin-2-one from starting material 8. In a first and critical reaction, starting material 8 is oxidized to 4-carboxyazetidin-2-one, compound 9. Herein this oxidation is conveniently carried out in a two phase reaction medium having a buffered aqueous phase emulsified by agitation with an organic phase. The organic phase may be chosen from tetrahydrofuran or acetone, but is preferably acetonitrile. To the aqueous phase is added a buffer such as $KH_2PO_4$. In the organic phase is starting material 8. With agitation and cooling, the oxidizing agents bromine and sodium chlorite are added in amounts appropriate to produce 4-carboxyazetidin-2-one. In the case of bromine, this amount is from about 2-150 mole % based on starting material 8 and preferably 5-15 mole %. In the case of sodium chlorite, this amount is from about 500-2000 mole % based on starting material 8. The presence of the sodium chlorite in combination with bromine is critical as too little sodium chlorite will result in an oxidation producing incomplete oxidation products regardless of the bromine employed. A preferred temperature for this first oxidation ranges from about 0° C. to about 20° C. for a time of from ½ to 10 hours.

The 4-carboxyazetidin-2-one 9 may subsequently be converted to the desired 4-carboxyazetidin-2-one 10 by standard electrochemical techniques. Contacting compound 9 in a polar organic solvent with a mixture of a $C_{1-8}$ organic acid and its alkali metal salt and applying a sufficient current density to the solution will substitute the 4-carboxy with an equivalent 4-acyloxy of the organic acid. Suitable $C_{1-8}$ organic acids include formic acid, acetic acid, benzoic acid etc. Suitable alkali metal salts are the sodium and potassium salts of these acids. Suitable polar organic solvents include acetonitrile, DMF, THF etc. For each mole of 4-carboxyazetidin-2-one, there might be employed about 2-5 moles of the alkali metal salt and similarly a gross excess of the acid, i.e. greater than 50 moles. A sufficient current density might range from about 2-20 mA/cm² and may be applied by an anode or cathode of carbon or platinum submerged in the solution. The electrochemical reaction is preferably carried out at from 0° C. to room temperature.

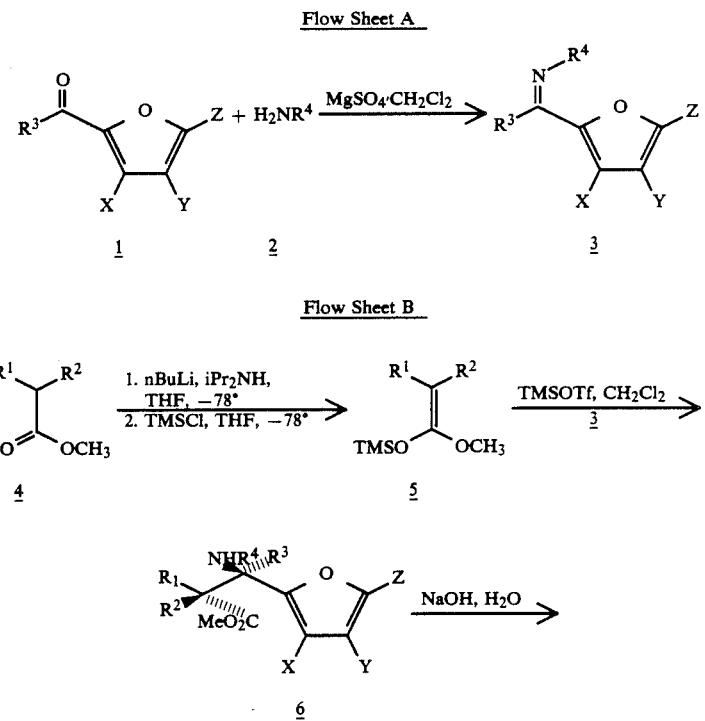

Flow Sheet C

Compound 10 may employed to make carbapenems or penems by well known methods. For example, 6-(1'-hydroxyethyl)-2-substituted-pen-2 em-3-carboxylic acid may be made from the above compounds as described in U.S. Pat. No. 4,260,618 hereby incorporated by reference. Therein, a 4-acyloxyazetidin-2-one is reacted with a substituted 1-thienoacetate derivative to provide a seco-lactam. Halogenation of the seco-lactam produces a compound which can be cyclized by treatment with a strong base to the penem. Further use of compound 10 to produce carbapenems are taught in Salzman, T. N., et al., J. Am. Chem. Soc., 1980, 102, 6161 and Reider, P. J., et al., Tetrahedron Lett., 1982, 23, 379.

The following examples are illustrative of the best mode of carrying out the instant invention as contemplated by us and should not be construed to be limitations on the spirit or scope of the instant invention.

EXAMPLE 1

(3R)-Z-1-Methoxy-1,3-bis-trimethylsilyloxy-1-butene 1.54M nBuLi (237 mL, 0.365 mol) was added to diisopropylamine (41.15 g, 0.407 mol) in dry THF (740 ml) at −78° C. under $N_2$. (R) Methyl 3-hydroxybutanoate, E1, (20.00 g, 0.169 mol) in THF (340 mL) was added dropwise such that the temperature did not rise above −71° C. After a 30 minute age chlorotrimethylsilane (40.5 g, 0.373 mol) in THF (100 mL) was added so as to maintain the temperature below −71° C. The solution was stirred at −78° C. for 2 hours, warmed to 0° C. and concentrated in vacuo Hexane (500 mL) was added and the mixture concentrated again. A second portion of hexane (500 mL) was added and the mixture was filtered and concentrated to a pale yellow oil (40.76 g). Distillation gave silyl ketene, E2, as a clear colorless oil b.p. 75°–80° C./0.25 mm (30.32 g, 79%).

EXAMPLE 2

(2S,3R,1"R)-Methyl 2-(1'-N-benzylamino-1'-(furan-2"-yl))-3-hydroxybutyrate

Furfural E3 (4,98 g, 51.8 mmol) was added to benzylamine E4 (5.55 g, 51.8 mmol) in $CH_2Cl_2$ (25 mL). $MgSO_4$ (5 g) was added and the mixture was stirred for hours, filtered and concentrated. The crude oil was redissolved in dry $CH_2Cl_2$ (60 mL) and concentrated repeatedly (2X) until the solution was dry (<10 mg $H_2O$/L). Trimethylsilyl trifluoromethanesulfonate (1.15 g, 5.18 mmol) was added to the imine above in $CH_2Cl_2$ (60 mL) at −20° C., after 5 minutes ketenesilylacetal, E2, (13.6 g, 51.8 mmol) was added and the solution aged for 18 hours. A second portion of ketenesilylacetal, E2, (3.6 g, 13.7 mmol) was added and the solution aged 16 hours. After warming to room temperature the solution was concentrated and redissolved in ethyl acetate (100 mL). The ethyl acetate solution was extracted with 2N HCl (50 mL); the aqueous solution was then treated with 5N $NH_4OH$ to give a pH>9 and was extracted with $CH_2Cl_2$ (50 mL). The $CH_2Cl_2$ solution was dried ($MgSO_4$) and concentrated to give amino ester, E5, as a yellow oil 13.78 g, 87.7%.

EXAMPLE 3

(2S,3R,1"R)-Methyl-Z-(1'-amino-1'-(furan-2"-yl))-3-hydroxybutyrate Hydrochloride

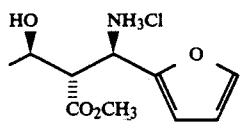   E6

12N HCl (0.48 mL, 5.76 mmol) and 10% Pd/C (170 mg) were added to the amino ester, E5, (1.75 g, 5.76 mmol) in methanol (17 mL). The mixture was hydrogenated at 1 psig $H_2$ at 25° C. until 98% of the starting material had been consumed (HPLC 1:1 $CH_3CN:H_2O$ (0.1% $H_3PO_4$), C8 column, 3 mL/min). The solution was filtered and concentrated to a white solid which was dissolved in 2-propanol (7 mL). Ethylether (30 mL) was then added dropwise with stirring to give hydrochloride, E6, as white needles which were collected on a filter, washed with 4:1 ether:2propanol (2×5 mL) and dried in vacuo (1.21 g, 79.5%).

EXAMPLE 4

(2S,3R,1"R)-2 (1'-Amino-1'-(furan-2"-yl))-3-hydroxybutyric acid

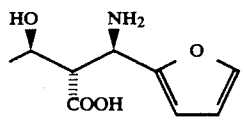   E7

The amino ester hydrochloride, E6, (55.69 g, 0.223 mol) was dissolved in $H_2O$ (225 mL). 5N NaOH was added to pH=12.5; the pH was maintained at pH 12.5 with a pH controller for 18 hours. The solution was then acidified to pH 2 and loaded onto a column of Dowex 50W×2 resin (700 mL). The column was washed with $H_2O$ (1400 mL) then eluted with 1.5N $NH_4OH$. The fractions containing the amino acid were concentrated in vacuo to a white solid. 2-Propanol (400 mL) was added and the mixture was concentrated to dryness. The resulting solid was stirred in 2-propanol (400 mL) for 16 hours, collected on a filter, and then dried in vacuo to give amino acid, E7, as an off-white solid (40.99 g, 92.2%).

EXAMPLE 5

(1"R,3S,4R)-3-(1"-Hydroxyethyl)-4(furan-2'-yl)azetidin-2-one

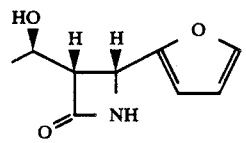   E8

$NaHCO_3$ (207.7 g, 2.47 mol) and then methanesulfonyl chloride (59.05 g, 0.51 mol) were added to dry 2-propanol (10.3L). The amino acid E7 (40.99 g, 0.206 mol) was added and the mixture was stirred at 25° C. under $N_2$ for 39 hours. The mixture was concentrated, and the resulting solid triturated in ethyl acetate (2.5 L). The mixture was filtered and concentrated to a yellow oil (60 g). The oil was dissolved in ethyl acetate (100 mL) stirred with charcoal (3.5 g), filtered and concentrated to 120 ml. Hexane was added to the cloud point and the solution was seeded, hexane (total of 45 mL) was added dropwise. The mixture was stirred at ambient temperature for 1 hour., filtered and the solid was washed with 1:1 hexane:ethyl acetate (2×15 mL) and dried (13.17 g, 35%). The mother liquor was filtered through a short column of silica gel eluting first with 1:1 hexane:ethyl acetate (500 mL) then 1:2 hexane:ethyl acetate (500 mL); the fractions containig the azetidinone were concentrated to an oil that solidified on standing. The solid was broken up and slurried in 1:1 hexane:ethyl acetate (30 mL), filtered, washed with the same solvent, (10 mL) and dried to give the desired azetidinone, E8, (11.31 g, 31%), total yield 66%

EXAMPLE 6

(1"R,3S,4R)-2 S(1"-t-Butyldimethylsilyloxyethyl)-4-(furan-2'-yl-azetidin-2-one

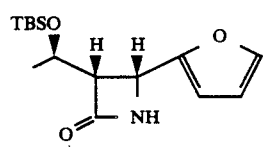   E9

Imidazole (5.63 g, 82.7 mmol) was added to 4-(furan-2-yl)-3-(1-hydroxyethyl)azetidin-2-one, E8, (10.00 g, 55.16 mmol) in dry DMF (25 mL). After cooling to 0° C., t-butyldimethylsilyl chloride (9.14 g, (60.67 mmol) was added, the cooling bath was removed and the solution was stirred at ambient temperature for 18 hours. Hexane:ethylacetate (1:1 75 mL) and water (50 mL) were added; the organic layer was washed with water (2×50 mL), dried (Mg $SO_4$), and concentrated to give the silyloxy azetidinone, E9, as a yellow oil (16.08 g, 98.6%).

EXAMPLE 7

ID:

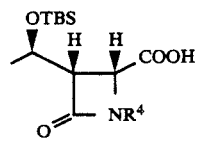   E10

Phosphate buffer was prepared from $KH_2PO_4$ (54.4 g), $H_3PO_4$ (1 mL), and $H_2O$ (500 mL). $NaClO_2$ (80%, 169 mg, 1.5 mmol) was added to the furanylazetidinone (295.6 mg, 1.00 mmol) in $CH_3CN$ (5 mL) and phosphate buffer (5 mL). The mixture was cooled to 0° C. and $Br_2$ (0.069 mL of 1.45M in $CH_3CN$, 0.1 mmol) was added. The temperature rose to 6° C., after recooling to 0° C. (about 3 min.) $NaClO_2$ (1.56 g, 13.8 mmol) was added and the mixture was stirred vigorously for 5 hours. Ethyl acetate (10 mL) and 10% $H_2SO_4$ (2 mL) were added and stirred for 5 min.; the aqueous layer was extracted with a second portion of ethyl acetate (5 mL) and the combined ethyl acetate solution was washed with 10% $Na_2S_2O_3$ (16 mL) giving a colorless solution. The $Na_2S_2O_3$ layer was extracted with ethyl acetate (5 mL) and the combined organic layer was dried ($MgSO_4$) and concentrated to a pale yellow oil (371 mg). Hexane: ethyl acetate (10:1, 2 mL) was added and the solution was seeded, after standing at ambient temperature for 2 hours 4-carboxyazetidin-2-one crystals were collected on a filter, were washed with 10:1 hexane: ethyl acetate (2×0.5 mL), and were dried in vacuo (107.5 mg, 39%).

EXAMPLE 8

(1″R,3R,4R) 3-(1″-t-Butyldimethylsilyoxyethyl)-4-acetoxyazetidin-2-one

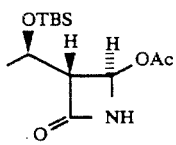
E11

Potassium acetate (6.5 g, 66 mmol) was added to 4-carboxyazetidin-2-one (5.0 g, 18.0 mmol) in 4:1 acetonitrile: acetic acid (350 mL) in an ESC electrochemical flow cell equipped with a stainless steel cathode and carbon felt anode. The solution was exposed to 5.5 mA/cm2 (1.1 amps at 3.3 to 3.8V) for 8.5 hours at 25° C. The solution was concentrated to 200 mL and then partitioned between water (200 mL) and ethyl acetate (100 mL), the aqueous layer was extracted with ethyl acetate (2×50 mL) and the combined organic layers were washed with saturated sodium bicarbonate solution (100 mL) and then brine (100 mL), dried (MgSO4) and concentrated to a solid. Silica gel chromatograhpy (4:1 hexane: ethyl acetate) gave pure 4(R)-acetyloxy-3(R)-[1(R)-dimethyl-1,1dimethylethylsilyloxyethyl-]azetidinone (3.82 g, 13.2 mmol, 73%).

What is claimed is:

1. A method for the production of 4-carboxyazetidin-2-one comprising the steps of:

(a) contacting, at temperatures from about 0°-20° C., an oxidizing combination of bromine and sufficient sodium chlorite to produce 4-carboxyazetidin-2one with a 4-furanyl compound of the formula

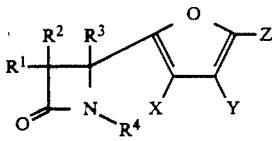

wherein $R^1$ and $R^2$ are independently selected from the group consisting of hydrogen, $C_{1-10}$ alkyl, $C_{1-10}$ fluoroalkyl, alpha-carbon substituted $C_{1-10}$ alkyl, alpha-carbon substituted $C_{1-10}$ fluoroalkyl, where the alpha-carbon substituent is selected from the group consisting of hydroxyl and protected hydroxyl; $R^3$ is selected from the group consisting of hydrogen and $C_{1-10}$ alkyl; $R^4$ is selected from the group consisting of hydrogen and a protecting group for nitrogen; and X, Y and Z are independently selected from the group consisting of hydrogen, halogen, $C_{1-10}$ alkyl, $C_6$ or $_{10}$ aryl, $C_{1-10}$ alkoxy, $C_6$ or $_{10}$ aryloxy.

2. The method of claim 1 wherein step (a) is followed by a step (i) contacting, in a polar organic solvent, said 4 carboxyazetidin-2-one with a mixture of a $C_{1-8}$ organic acid and its corresponding alkali metal salt under sufficient current density to produce 4-acyloxyazetidin-2-one.

3. The method of claim 1 wherein $R^4$ is hydrogen.

4. The method of claim 1 wherein said oxidizing combination comprises from about 5 to about 15 mole % bromine based on said 4-furanyl compound.

5. The method of claim 1 wherein said oxidizing combination :comprises from about 2 to about 150 mole % bromine based on said 4 furanyl compound.

6. The method of claim 1 wherein said oxidizing combination comprises from about 500 to about 2000 mole % sodium chlorite based on said 4-furanyl compound.

7. The method of claim 1 wherein $R^1$ or $R^2$ is hydrogen.

8. The method of claim 1 wherein $R^2$ is beta-hydrogen and $R^1$ is other than hydrogen.

9. The method of claim 1 wherein $R^2$ is beta-hydrogen and $R^1$ is alpha oriented 1-hydroxyethyl.

10. The method of claim 1 wherein X, Y and Z are hydrogen.

* * * * *